United States Patent
Oyama et al.

(10) Patent No.: US 11,426,145 B2
(45) Date of Patent: Aug. 30, 2022

(54) ULTRASONIC DIAGNOSTIC APPARATUS, TRACING METHOD, AND PROGRAM

(71) Applicant: Hitachi, Ltd., Tokyo (JP)

(72) Inventors: Seiji Oyama, Tokyo (JP); Kazumasa Ise, Tokyo (JP)

(73) Assignee: FUJIFILM HEALTHCARE CORPORATION, Kashiwa (JP)

( * ) Notice: Subject to any disclaimer, the term of this patent is extended or adjusted under 35 U.S.C. 154(b) by 108 days.

(21) Appl. No.: 16/812,639

(22) Filed: Mar. 9, 2020

(65) Prior Publication Data
US 2020/0305844 A1 Oct. 1, 2020

(30) Foreign Application Priority Data

Mar. 27, 2019 (JP) .............................. JP2019-060111

(51) Int. Cl.
| | | |
|---|---|---|
| *A61B 8/08* | (2006.01) | |
| *A61B 8/00* | (2006.01) | |
| *A61B 8/06* | (2006.01) | |

(52) U.S. Cl.
CPC ................ *A61B 8/488* (2013.01); *A61B 8/06* (2013.01); *A61B 8/0858* (2013.01); *A61B 8/5223* (2013.01); *A61B 8/543* (2013.01)

(58) Field of Classification Search
CPC ......... A61B 8/488; A61B 8/06; A61B 8/0858; A61B 8/5223; A61B 8/543; A61B 8/486; A61B 8/0883; A61B 8/5246
See application file for complete search history.

(56) References Cited

U.S. PATENT DOCUMENTS

| | | | | |
|---|---|---|---|---|
| 5,868,676 A | * | 2/1999 | McCabe | ................... A61B 8/06 600/454 |
| 2010/0234731 A1 | * | 9/2010 | Lu | ........................ G01S 7/52066 600/454 |

FOREIGN PATENT DOCUMENTS

JP H07-241289 A 9/1995

* cited by examiner

*Primary Examiner* — Bo Joseph Peng
(74) *Attorney, Agent, or Firm* — Foley & Lardner LLP (57) ABSTRACT

To correctly trace a target component even when a folded component is included in a Doppler waveform. The Doppler waveform is configured by a plurality of luminance distributions 54 arranged on a time axis. In each luminance distribution 54, a minimum luminance value located in the trough portion 54c between the target portion 54a and the folded portion 54b is specified. A search start point Pn is set based on the minimum luminance value. A trace point 60 is specified by searching from the search start point Pn to a base line 61 side.

2 Claims, 7 Drawing Sheets

ULTRASONIC DIAGNOSTIC APPARATUS, TRACING METHOD, AND PROGRAM

TECHNICAL FIELD

The present invention relates to an ultrasonic diagnostic apparatus, a tracing method, and a program, and more particularly, to a technique of tracing a Doppler waveform.

BACKGROUND ART

Generally, an ultrasonic diagnostic apparatus includes a Doppler mode for generating a Doppler waveform. The Doppler waveform shows a time change in Doppler information on a moving body (blood flow or the like) of a living body. Specifically, for the Doppler waveform, a horizontal axis is a time axis, and a vertical axis is a frequency axis (velocity axis). The Doppler waveform is configured by a plurality of luminance distributions arranged on the time axis. Each luminance distribution shows a velocity distribution, that is, a frequency spectrum calculated based on Doppler information. Each luminance which constitutes the luminance distribution corresponds to power of each velocity component. As the Doppler waveform, a blood flow Doppler waveform and a tissue Doppler waveform are known. The latter tissue Doppler waveform shows, for example, motion information of a myocardium. As the Doppler mode, a pulse Doppler mode (PW mode) to which a pulse Doppler method is applied and a continuous wave Doppler mode (CW mode) to which a continuous wave Doppler method is applied are known.

Before analysis and measurement of the Doppler waveform, the Doppler waveform is traced as necessary. The trace includes a manual trace and an automatic trace. In the automatic trace, for example, among luminance distributions, a point which satisfies a predetermined condition on a high frequency side (non-base line side) than a peak as an apex is specified as a trace point.

A folding phenomenon may occur in the Doppler waveform generated in the pulse Doppler mode. An observable velocity range is defined depending on a transmission pulse repetition period (PRT). When there is a velocity component which exceeds the velocity range on a positive side or a negative side, the velocity component is displayed as a folded component. When the Doppler waveform is displayed, a function called base line shift can be used. That is, a base line corresponding to velocity 0 is shifted to the positive side or the negative side. Even when the base line shift is performed, a size of the velocity range itself does not change, and it is difficult to avoid all folding phenomena by the base line shift.

PRIOR ART LITERATURE

Patent Literature

PTL 1: JP-A-7-241289

SUMMARY OF INVENTION

Technical Problem

It is desirable to correctly trace the Doppler waveform even when the folded component is included in the Doppler waveform. PTL 1 discloses a technique of tracing a Doppler waveform. In the technique, the Doppler waveform is traced with a folded component being removed.

An object of the present disclosure is to improve the accuracy of tracing the Doppler waveform which includes the folded component. Alternatively, an object of the present disclosure is to execute a tracing method adapted to nature of the Doppler waveform.

Solution to Problem

An ultrasonic diagnostic apparatus according to the present disclosure includes: a Doppler waveform generation unit configured to generate a Doppler waveform based on Doppler information obtained by transmitting and receiving an ultrasonic wave; and a trace unit configured to specify, based on the Doppler waveform, a trace point for each of luminance distributions which constitute the Doppler waveform, in which the trace unit includes: a reference point setting unit which sets a reference point in a trough portion between a target portion and a folded portion included in the luminance distributions; and a search unit which searches for the trace point on a base line side of the reference point in the luminance distributions.

A tracing method according to the present disclosure includes: a step of specifying, based on a first Doppler waveform generated from first Doppler information obtained by transmitting and receiving a first ultrasonic wave, a first trace point for each of first luminance distributions which constitute the first Doppler waveform; and a step of specifying, based on a second Doppler waveform generated from second Doppler information obtained by transmitting and receiving a second ultrasonic wave, a second trace point for each of second luminance distributions which constitute the second Doppler waveform, in which in the step of specifying the first trace point, a search start point is set in a trough portion between a target portion and a folded portion included in the first luminance distributions, and the first trace point is searched for from the search start point to abase line side in the first luminance distributions, and in the step of specifying the second trace point, the second trace point is searched for from an end point on an opposite side of the base line to the base line side in the second luminance distributions.

A program according to the present disclosure is a program executed by an information processing apparatus, the program including a function of specifying, based on a Doppler waveform generated from Doppler information obtained by transmitting and receiving an ultrasonic wave, a trace point for each of luminance distributions which constitute the Doppler waveform, in which the function includes: a function of setting a search start point in a trough portion between a target portion and a folded portion included in the luminance distributions; and a function of searching for the trace point from the search start point to a base line side in the luminance distributions.

Advantageous Effect

According to the invention, the accuracy of tracing the Doppler waveform which includes the folded component can be improved. Alternatively, according to the invention, the tracing method adapted to the nature of the Doppler waveform can be executed.

DESCRIPTION OF EMBODIMENTS

Hereinafter, an embodiment will be described with reference to the drawings.

(1) Outline of Embodiment

An ultrasonic diagnostic apparatus according to the embodiment includes a Doppler waveform generation unit and a trace unit. The Doppler waveform generation unit is configured to generate a Doppler waveform based on Doppler information obtained by transmitting and receiving an ultrasonic wave. The trace unit is configured to specify, based on the Doppler waveform, a trace point for each of luminance distributions which constitute the Doppler waveform. Specifically, the trace unit includes a reference point setting unit and a search unit. The reference point setting unit is configured to set a reference point in a trough portion between a target portion and a folded portion included in the luminance distributions. The search unit is configured to search for the trace point on a base line side of the reference point in the luminance distributions.

According to the above configuration, since the trace point is searched for on the base line side from the reference point in the trough portion, the trace point can be searched for with the folded portion being avoided. Therefore, it can be avoided to set the trace point in the folded portion. The trough portion is a portion which includes a lower apex (or a point having a minimum value), and corresponds to a bottom portion. The Doppler waveform is a blood flow Doppler waveform in a specific example described later. When the blood flow Doppler waveform and a tissue Doppler waveform are simultaneously displayed, a transmission pulse repetition period becomes large, and the folding phenomenon easily occurs in the blood flow Doppler waveform. Therefore, in that case, it is highly necessary to adopt the above configuration.

The description of the above configuration describes the function of the trace unit when the folded portion occurs. When the folded portion does not occur, an entire non-base line side of the target portion corresponds to the trough portion or the bottom portion, and the reference point is set therein. Regardless of presence or absence of the folded portion, the same trace algorithm is preferably applied to the luminance distributions. From this point of view, it is preferable to detect the reference point within a detection range determined in accordance with a predetermined condition, as will be described later. The detection range corresponds to a window for narrowing the trough portion or a portion which includes the trough portion as a processing target.

In the embodiment, the reference point is a search start point, in which case, the reference point setting unit is a search start point setting unit. According to the configuration, it is possible to reliably search for the trace point while avoiding the folded portion.

In the embodiment, the reference point setting unit includes a range setting unit configured to set the detection range in which a current search start point is detected based on a past search start point. Accordingly, the detection range is determined using continuity of the Doppler waveform in a time axis direction. According to the configuration, the search start point can be quickly detected, and an amount of calculation can be reduced accordingly. In addition, a possibility that the search start point is erroneously detected can be reduced. The past search start point is, for example, a previous search start point.

In the embodiment, the search unit sets the current search start point by specifying a minimum luminance value within the detection range. A point (minimum value point) having the minimum luminance value within the detection range corresponds to the apex in the trough portion. The point is the boundary between the target portion and the folded portion, or the reference point for dividing the target portion and the folded portion. In the above configuration, search of the trace point is performed from the reference point as a starting point to the base line side. When a plurality of minimum value points is specified, an intermediate point among the minimum value points, a highest frequency side point among the minimum value points, or the like may be used as the search start point. At this time, an arrangement state of the plurality of minimum value points may be considered.

A tracing method according to the embodiment includes a first step and a second step. The first step is a step of specifying, based on a first Doppler waveform, a first trace point for each of first luminance distributions which constitute the first Doppler waveform generated based on first Doppler information obtained by transmitting and receiving a first ultrasonic wave. The second step is a step of specifying, based on a second Doppler waveform, a second trace point for each of second luminance distributions which constitute the second Doppler waveform generated based on second Doppler information obtained by transmitting and receiving a second ultrasonic wave. In the first step, a search start point is set in a trough portion between a target portion and a folded portion included in the first luminance distributions, and the first trace point is searched for from the search start point to a base line side in the first luminance distributions. In the second step, the second trace point is searched for from an end point on an opposite side of the base line to the base line side in the second luminance distributions.

For example, the first Doppler waveform is a Doppler waveform having a high possibility of including a folded component, and the second Doppler waveform is a Doppler waveform having a low possibility of including a folded component. For the first Doppler waveform, the search start point is set in the trough portion so that the trace point is not specified in the folded portion, and the first trace point is searched for from the search start point to the base line side. For the second Doppler waveform, the second trace point is searched for from the end point on the opposite side of the base line to the base line side. According to the configuration, the amount of calculation can be reduced and it is possible to quickly search for the trace points. According to the above configuration, the tracing method is changed based on nature of the Doppler waveform, particularly in accordance with the possibility of including a folded portion.

In the embodiment, the first Doppler waveform is the blood flow Doppler waveform, and the second Doppler waveform is the tissue Doppler waveform. A plurality of blood flow Doppler waveforms maybe displayed. In that case, the tracing method that is less likely to be affected by the folded component is applied to both of the Doppler waveforms.

The tracing method according to the embodiment includes a function of specifying, based on the Doppler waveform, the trace point for each of the luminance distributions which constitute the Doppler waveform generated based on the Doppler information obtained by transmitting and receiving the ultrasonic wave. The function includes a function of setting the search start point in the trough portion between the target portion and the folded portion included in the luminance distributions, and a function of searching for the trace point from the search start point to the base line side in the luminance distributions.

The above method is implemented as a function of hardware or as a function of software. In the latter case, a program that implements the function is installed in an information processing apparatus. A concept of the information processing apparatus includes a computer, the ultrasonic diagnostic apparatus and the like.

(2) Detailed Description of Embodiment

Figure 1:
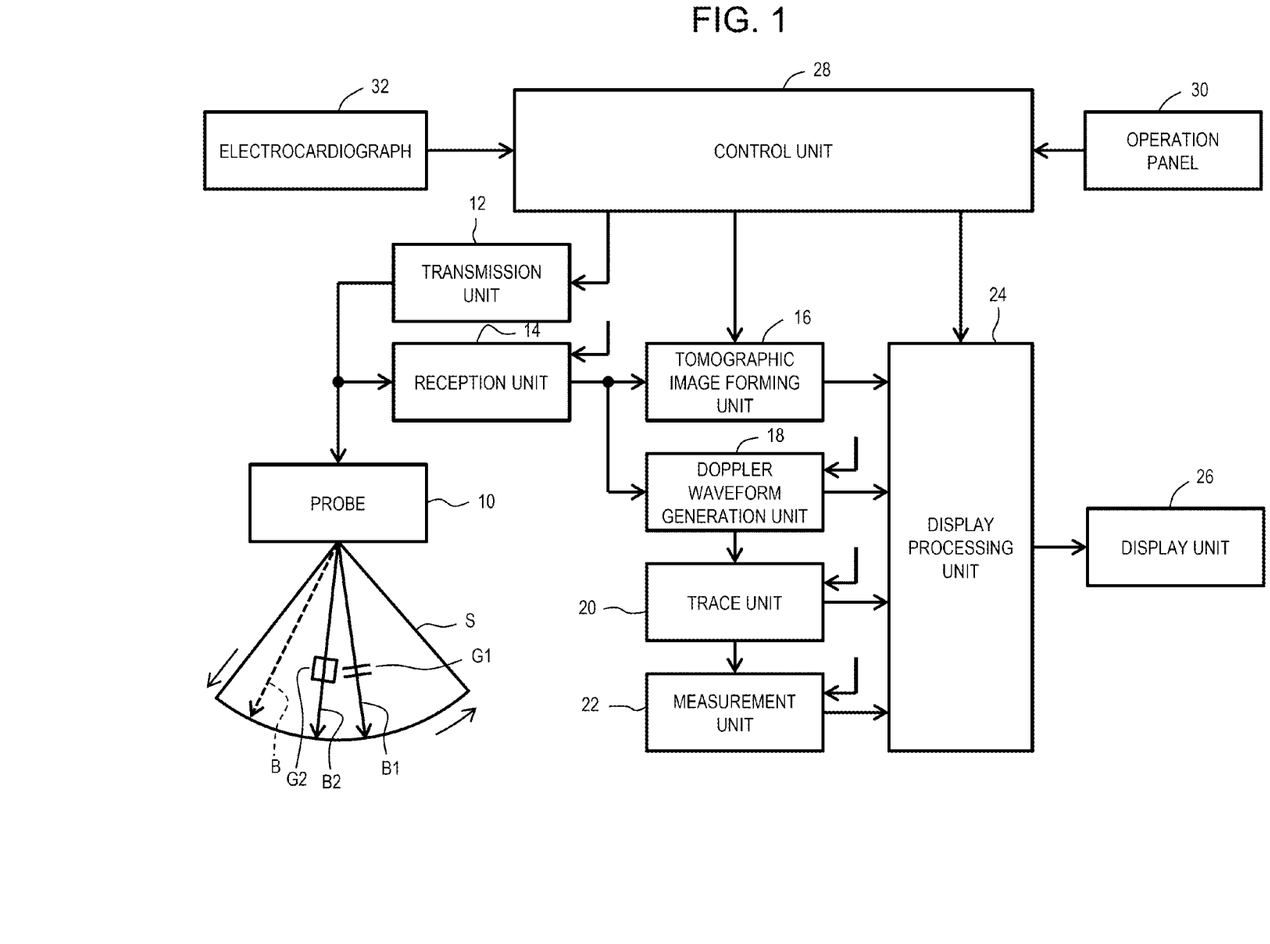
FIG. 1 is a block diagram showing a configuration example of an ultrasonic diagnostic apparatus according to an embodiment.

FIG. 1 is a block diagram of the ultrasonic diagnostic apparatus according to the embodiment. The ultrasonic diagnostic apparatus is a medical apparatus which generates an ultrasonic image based on received information obtained by transmitting and receiving an ultrasonic wave to and from a living body, and displays the ultrasonic image. In the embodiment, a tomographic image and a Doppler waveform are displayed as the ultrasonic image.

In FIG. 1, a probe 10 transmits and receives an ultrasonic wave in a state of being in contact with a surface of a test object as the living body. A vibration element array is provided in the probe 10. The vibration element array includes a plurality of vibration elements arranged in a straight line or an arc shape. When a B mode is executed, the vibration element array forms an ultrasonic beam B. The ultrasonic beam B is used for electronic scanning. Accordingly, a scanning surface S is formed. As an electronic scanning method, electronic sector scanning, electronic linear scanning and the like are known.

When a pulse Doppler mode (PW mode) is executed, the ultrasonic beam is repeatedly formed in a direction designated by a user. Two ultrasonic beams may be alternately formed in two directions. In the example shown in FIG. 1, an ultrasonic beam B1 for observing blood flow Doppler information and an ultrasonic beam B2 for observing tissue Doppler information are shown. A sample gate G1 which extracts blood flow Doppler information is set on the ultrasonic beam B1, and a sample gate G2 which extracts tissue Doppler information is set on the ultrasonic beam B2. The tissue is, for example, a myocardium as a moving soft tissue.

A mode in which the B mode and the PW mode are executed simultaneously is also referred to as a composite mode. A transmission and reception sequence of the composite mode is usually configured by a plurality of sequence units arranged on the time axis. In other words, a subsequence having a specific configuration is repeatedly executed on the time axis. The subsequence is configured by, for example, a plurality of times of B mode transmission and reception, and one Doppler transmission and reception which are arranged on the time axis. In the composite mode in which a plurality of Doppler beams are formed, the subsequence is configured by, for example, a plurality of times of B mode transmission and reception, one first Doppler transmission and reception, and one second Doppler transmission and reception which are arranged on the time axis. The first Doppler transmission and reception are transmission and reception for acquiring blood flow Doppler information as the first Doppler information. The second Doppler transmission and reception are transmission and reception for acquiring tissue Doppler information as the second Doppler information.

A transmission unit 12 is an electronic circuit that functions as a transmission beam former. At the time of transmission, a plurality of transmission signals is supplied in parallel from the transmission unit 12 to the vibration element array. A reception unit 14 is an electronic circuit that functions as a reception beam former. At the time of reception, a plurality of reception signals is output in parallel from the vibration element array to the reception unit 14. In the reception unit 14, phasing addition is applied to a plurality of reception signals, and accordingly, beam data is generated. By repeating the transmission and reception for the B mode, frame data corresponding to the scanning surface is sequentially generated. Each frame data includes a plurality of beam data arranged in an electronic scanning direction. Each beam data includes a plurality of echo data arranged in a depth direction. Each frame data is sent to a tomographic image forming unit 16. The plurality of beam data acquired by repetition of transmission and reception for the Doppler mode is sequentially sent to the Doppler waveform generation unit.

The tomographic image forming unit 16 is an electronic circuit that forms a tomographic image based on input frame data. The tomographic image forming unit 16 includes a digital scan converter (DSC). The DSC has a coordinate conversion function, a pixel interpolation function, a frame rate conversion function and the like. Data of the tomographic image is sent to a display processing unit 24.

A Doppler waveform generation unit 18 is an electronic circuit that generates a Doppler waveform based on Doppler information included in the beam data. In the embodiment, the Doppler waveform generation unit 18 includes a gate circuit, an FFT calculation circuit and the like. Data of the Doppler waveform is sent to the display processing unit 24.

A trace unit 20 functions as a trace device, and is an electronic circuit that generates a trace line by applying the tracing processing to the Doppler waveform. The trace unit 20 functions as a reference point setting unit (specifically, a search start point setting unit) and a search unit. The configuration and operation of the trace unit 20 will be described in detail later. Data of the trace line is sent to the display processing unit 24.

The tracing processing executed by the trace unit 20 is executed on the Doppler waveform within a predetermined period set based on an electrocardiogram waveform. Specifically, a waveform portion within the predetermined period is cut out from the Doppler waveform as a still image, and the tracing processing is applied to the waveform portion. The tracing processing may be applied to an entire Doppler waveform generated in real time. The measurement unit 22 is an electronic circuit that executes measurement based on the trace line. The measurement includes time measurement and the like. A measurement result is sent to the display processing unit 24.

Before the tracing processing, a smoothing processing is applied to the entire Doppler waveform or the waveform portion cut out from the Doppler waveform. A threshold value to be described later is determined based on the smoothed Doppler waveform or the smoothed waveform portion. In the smoothing processing, for example, a two-dimensional smoothing filter is used. Generally, each processing for generating the trace line does not affect the displayed Doppler waveform. The trace line, as a tracing processing result, is superimposed on the displayed Doppler waveform.

The display processing unit 24 is an electronic circuit that has an image composition function, a color processing function and the like. The display processing unit 24 generates an image to be displayed on a display unit 26. The display unit 26 includes a liquid crystal display unit, an organic EL display unit and the like. A module which includes the tomographic image forming unit 16, the Doppler waveform generation unit 18, the trace unit 20, the measurement unit 22, and the display processing unit 24 may be configured by one or a plurality of processors. The module may be configured by another device (for example, an information processing apparatus). A control unit 28 described below may execute each of the functions described above.

The control unit 28 controls operations of each element shown in FIG. 1. The control unit 28 is configured by a CPU which executes an operation program. The control unit 28 is connected to an operation panel 30. The operation panel 30 includes a plurality of switches, a keyboard, a trackball and the like. The operation panel 30 is used by a user to select an operation mode, and to set a Doppler observation direction and a gate.

An electrocardiograph 32 is a measurement device which has a plurality of electrodes attached to the test object and acquires an electrocardiographic signal (ECG signal). The electrocardiographic signal is input to the control unit 28. The electrocardiographic signal is referred to by the control unit 28 and the trace unit 20. In the embodiment, the electrocardiographic signal is referred to define the waveform portion to be subjected to the tracing processing in the Doppler waveform. In that case, an R wave or the like is used as a time phase reference.

Figure 2:
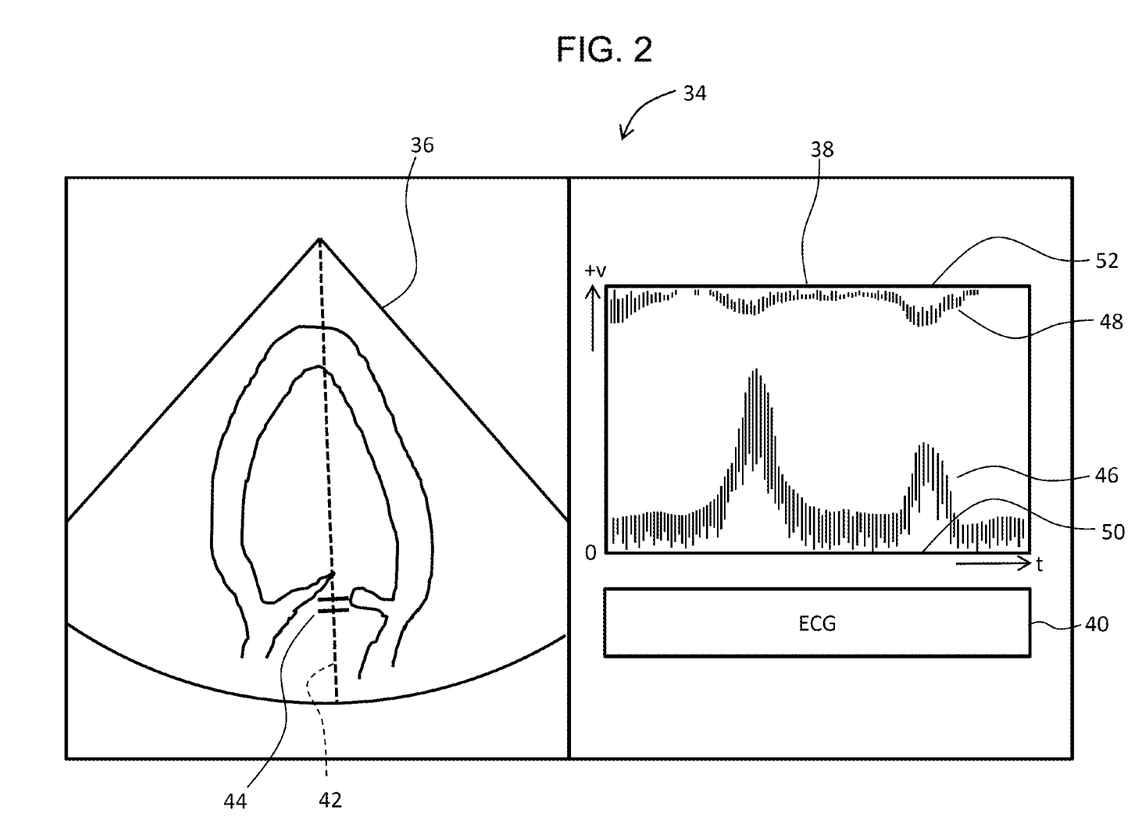
FIG. 2 is a diagram showing a display image before tracing.

FIG. 2 shows a display image 34 before tracing. The display image 34 is an image displayed on a display screen of a display unit. The display image 34 includes a tomographic image 36 and a Doppler waveform (specifically, a blood flow Doppler waveform) 38. The display image 34 also includes an electrocardiographic signal waveform 40. Specifically, the tomographic image 36 is an image showing a cross section of a left ventricle of a heart. A gate marker 44 indicating a gate position is displayed on a direction marker 42. Doppler information corresponding to the gate position is sequentially extracted from the plurality of received signals, and the Doppler waveform 38 is generated by performing frequency analysis on Doppler information.

The Doppler waveform 38 includes a target component 46 and a folded component 48. In an illustrated example, a base line 50 is at a lower side in a display frame of the Doppler waveform 38. The base line 50 is a line corresponding to velocity 0. The horizontal axis is the time axis, and the vertical axis shows a Doppler shift frequency, that is, velocity. In practice, the illustrated vertical axis is a positive velocity axis. In the illustrated example, a negative velocity component appears as a folded component 48 on a top portion of the Doppler waveform 38. When an actual velocity exceeds a positive side and a negative side of an observable velocity range, the folding phenomenon occurs. Incidentally, an upper side 52 corresponds to the maximum flow rate of the observable velocity range.

When the tracing processing is applied to such a Doppler waveform without considering the folded component 48, not only the target component 46 but also the folded component 48 may be traced. Therefore, in the present embodiment, a tracing processing is executed in which the target component 46 can be traced without being affected by the folded component 48 even if the folded component 48 occurs. The will be described in detail with reference to FIG. 3. The Doppler waveform to be traced (exactly the waveform portion) is cut out based on the electrocardiographic signal as already described.

Figure 3:
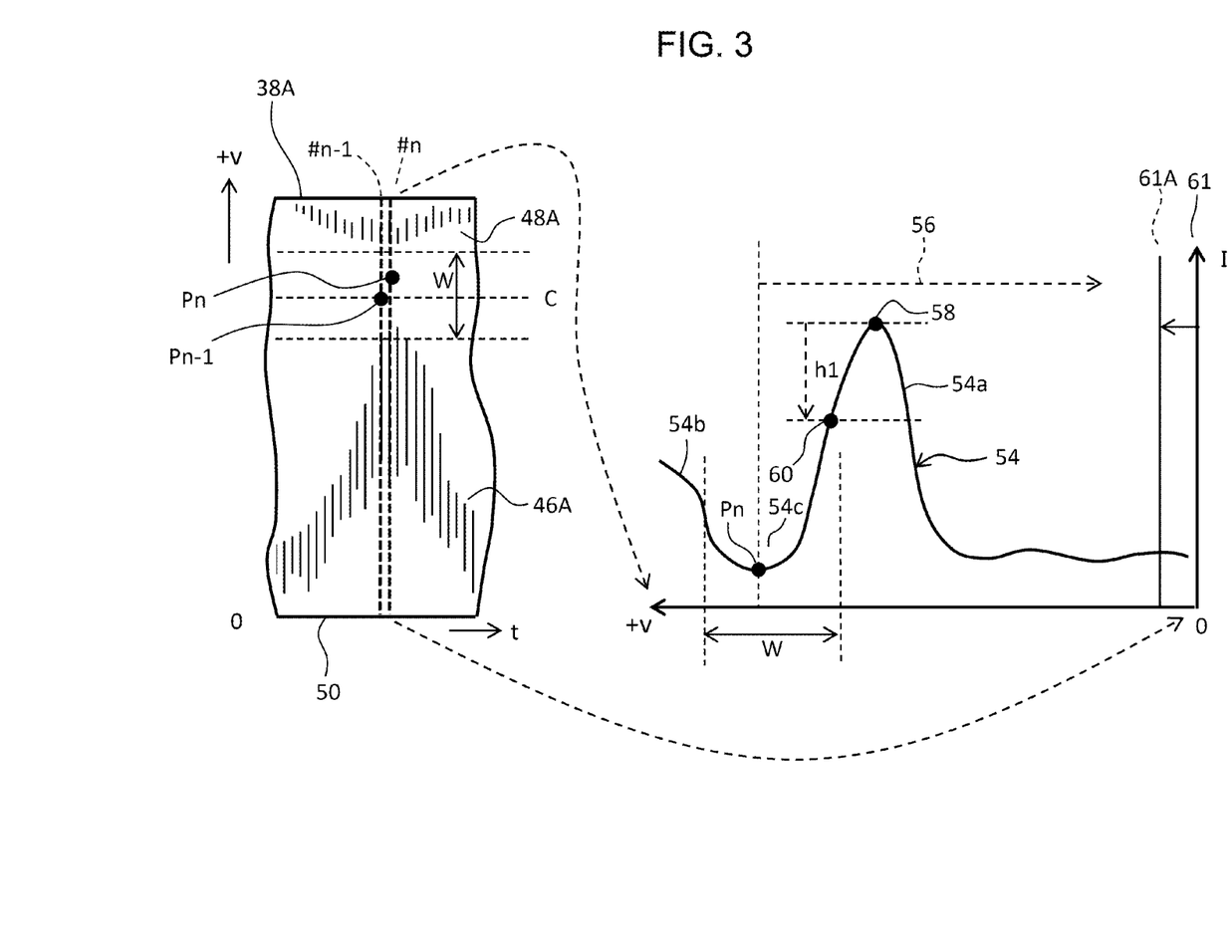
FIG. 3 is a diagram showing a trace point search processing.

In FIG. 3, a portion 38A of the blood flow Doppler waveform is shown on the right side. The portion 38A includes a target component portion 46A and a folded component portion 48A. The base line 50 is at a lower side. A line on which the previous trace point search is performed is indicated by #n−1, and a line on which the current trace point search is performed is indicated by #n. A point having the lowest luminance value (minimum value point) in line #n−1 is a previous search start point Pn−1. A section having a constant width in the vertical axis direction is determined with the position of the previous search start point C as a center. The section is a detection range W for the line #n. This is how to use a previous reference point (specifically, the search start point) in detection of a current reference point (specifically, the search start point) based on the continuity of the Doppler waveform in the time axis direction. In a first line, it is preferable to preset a detection range. Depending on the nature of the Doppler waveform, a plurality of detection ranges set for a plurality of lines may be the same.

In FIG. 3, a luminance distribution 54 corresponding to the line #n is shown on the right side. The horizontal axis is the positive velocity axis. The vertical axis is a luminance axis. A reference numeral 61 indicates a base line position. In the illustrated example, the base line position matches with a position of the vertical axis. It is possible to change a position of the base line, and for example, it is also possible to move the base line to a position indicated by a reference numeral 61A.

In the illustrated example, the luminance distribution 54 includes a target portion 54a and a folded portion 54b, and a trough portion 54c is located therebetween. The lowest luminance value is specified in the detection range W, and a point (minimum value point) having the lowest luminance value is specified. The minimum value point corresponds to a downward apex in the trough portion 54c, and is set as a search start point Pn in the embodiment. The search start point Pn functions as a reference point of search. The search start point Pn may be determined based on another reference point in the trough portion 54c. It is preferable to determine the search start point or an upper end point of a search range at least on the base line 61 side of the folded portion 54b so that a main portion of a slope between the trough portion 54c and a peak 58 is included in a trace point search range.

In the embodiment, a trace point search is executed from the search start point Pn to the base line 61 in units of pixels (see reference numeral 56). In that case, for example, when a luminance value exceeding the threshold value is first found, the point having the luminance value is determined as a trace point 60. The threshold value is determined based on the Doppler waveform subjected to the smoothing processing or the waveform portion subjected to the smoothing processing, and is determined based on, for example, a noise level average value. The threshold value may be determined based on an average luminance value. A level of the peak 58 may be specified and the threshold value may be determined based on the level. For example, a level which is lower than the level of the peak 58 by a certain percentage h1 may be determined as the threshold value. Generally, a point corresponding to an upper edge or an upper end of the target portion 54a is determined as the trace point.

The above processing is executed for each line, that is, for each luminance distribution. Accordingly, the trace line is constituted by a plurality of specified trace points. The trace line may be configured by applying a spline interpolation processing or the like to the plurality of trace points.

Figure 4:
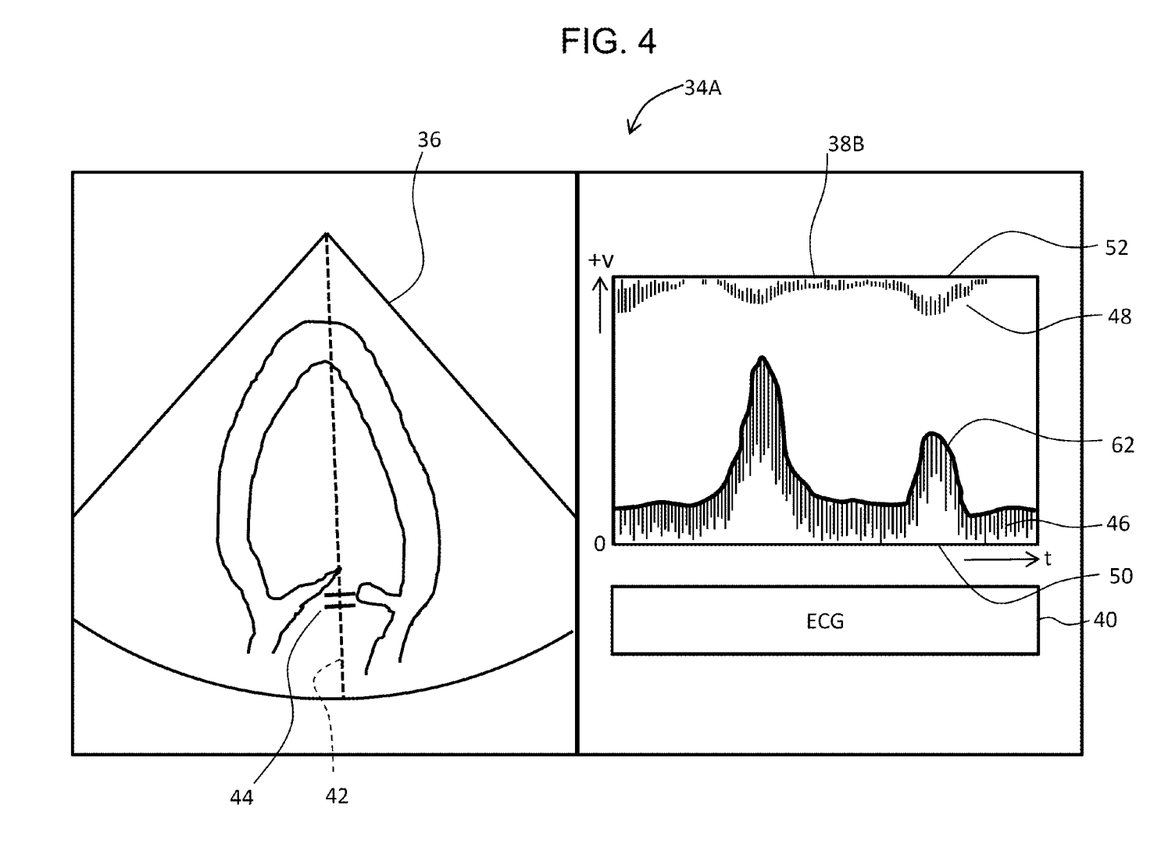
FIG. 4 is a diagram showing a display image after the tracing.

FIG. 4 shows the display image 34A after the tracing. The elements already described are denoted by the same reference numerals, and the description thereof is omitted. Similarly, this also applies to other drawings described below.

In FIG. 4, a Doppler waveform 38B includes a trace line 62. The trace line 62 is drawn along a contour of the target component 46, and a trace with respect to a contour of the folded component 48 is avoided. When a trace point determination condition is changed, a position or a shape of the trace line 62 is changed, but even in such a case, according to the embodiment, it is possible for the folded component 48 to avoid being traced.

Figure 5:
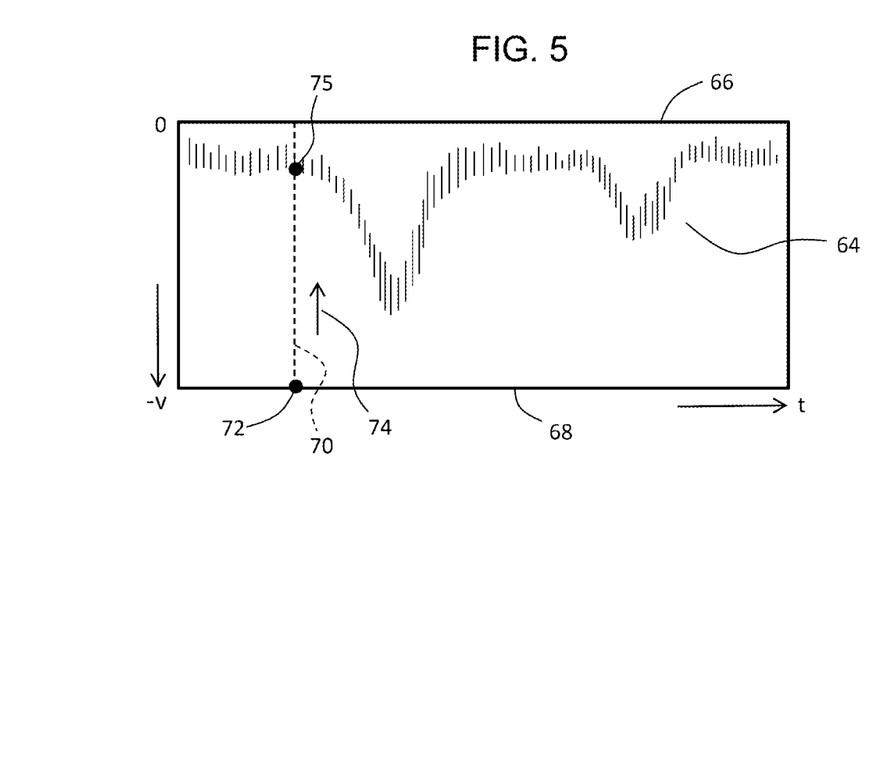
FIG. 5 is a diagram showing another tracing processing.

FIG. 5 shows another Doppler waveform. A Doppler waveform 64 is the tissue Doppler waveform. The horizontal axis is the time axis, and the vertical axis is a negative velocity axis. An upper side of the display frame is a base line 66. A lower side 68 of the display frame corresponds to an observable negative maximum flow rate. The Doppler waveform 64 includes only the target component, and the folded component is not observed in the Doppler waveform 64. When such a Doppler waveform 64 is traced, a search start point 72 in each line 70 is set on the lower side 68, and a trace point is searched for from the search start point 72 to the base line 66 side (see reference numeral 74). When a luminance value which matches or exceeds a predetermined threshold value is found, a position of the luminance value is determined as a trace point 75. When there is no folded portion, it is preferable to perform a simple trace point search as described above from the viewpoint of reducing the amount of calculation and shortening calculation time.

Figure 6:
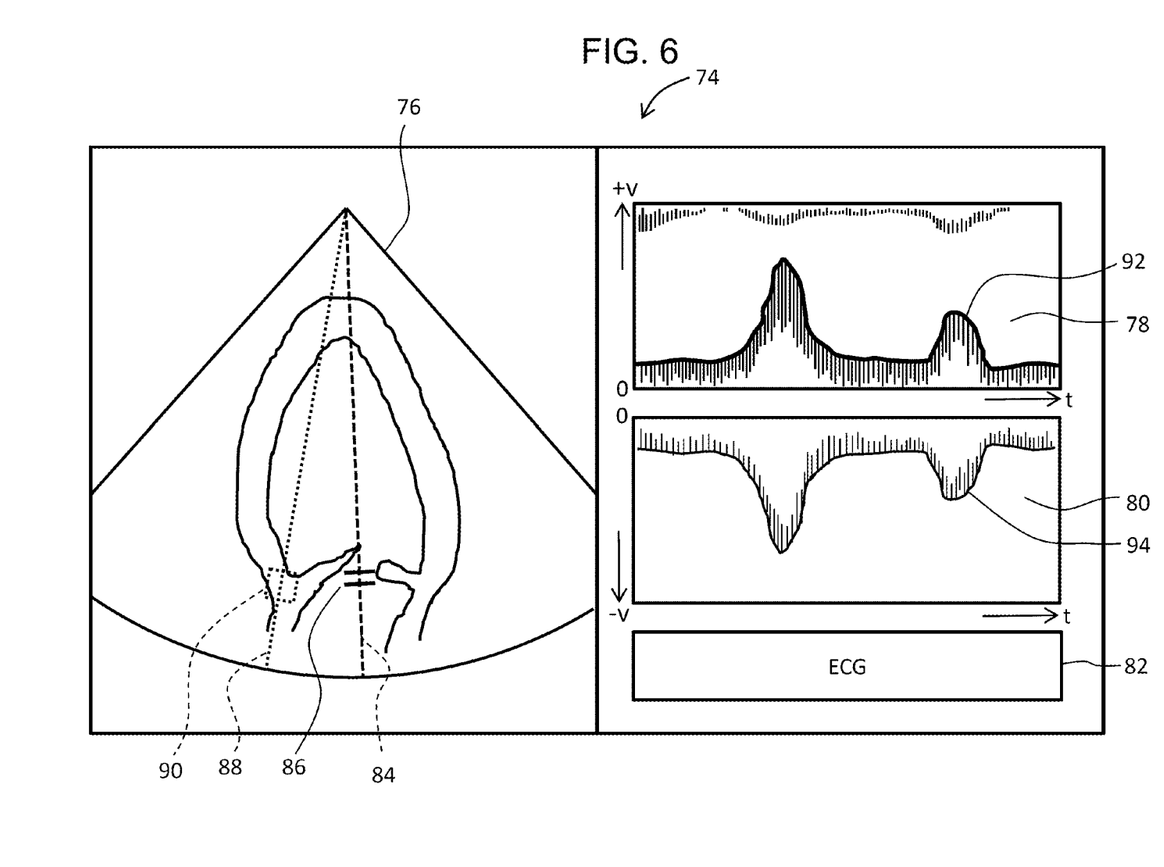
FIG. 6 is a diagram showing a display image including two Doppler waveforms.

FIG. 6 shows a display image 74 after the tracing. A tomographic image 76 includes a direction line 84 and a direction line 88. A blood flow sample gate 86 is set on the direction line 84, and a tissue sample gate 90 is set on the direction line 88.

The display image 74 includes a blood flow Doppler waveform 78, a tissue Doppler waveform 80, and an electrocardiographic signal waveform 82. The blood flow Doppler waveform 78 includes a trace line 92 created by the method shown in FIG. 3, and the tissue Doppler waveform 80 includes a trace line 94 created by the method shown in FIG. 5.

Figure 7:
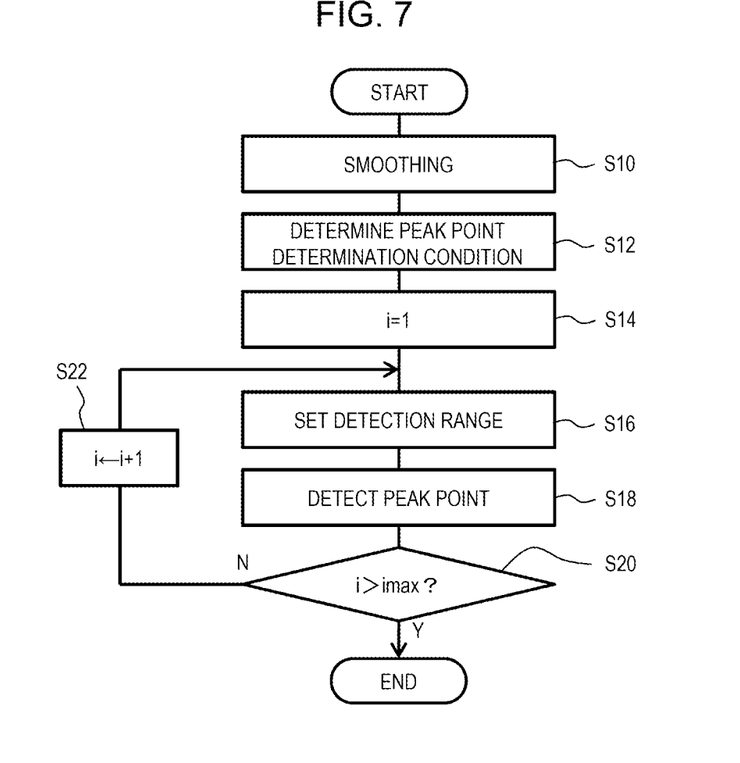
FIG. 7 is a flowchart showing the trace point search processing.

FIG. 7 is a flowchart showing the tracing processing according to the embodiment. The tracing processing is performed for the blood flow Doppler waveform. In S10, the waveform portion within a predetermined period is cut out from the Doppler waveform based on the electrocardiographic signal, and the waveform portion is smoothed. Here, the waveform portion is also referred to as the Doppler waveform for convenience. In S12, a peak determination condition is determined based on the Doppler waveform. For example, the threshold value as the peak determination condition is determined based on an average luminance of a noise portion included in the Doppler waveform. The threshold value may be determined based on the average luminance of the entire Doppler waveform, or the threshold value may be determined based on a peak of the target portion. In S14, a line number i is initialized. In S16, the detection range is set on an i-th line based on an (i−1)-th search start point. In S18, a point having the minimum luminance value (the minimum value point) within the detection range on the n-th line is determined as the search start point. In the luminance distribution, luminance values are sequentially referred to in a base line direction from the search start point, and a peak point is determined at a position having the luminance value when the luminance value equal to or more than the threshold value is found. When i equals to 1, there is no search start point therebefore, and therefore, the minimum value point is detected within a detection range designated as a default.

In S20, it is determined whether i exceeds the maximum value, when i does not exceed the maximum value, i is incremented by 1 in S22, and the steps after S16 are executed. The above processing is executed in unit of line, that is, for each luminance distribution, and finally, a trace line is formed by arranging a plurality of trace points. A trace line may be configured by an approximate curve generation processing based on the plurality of trace points.

Figure 8:
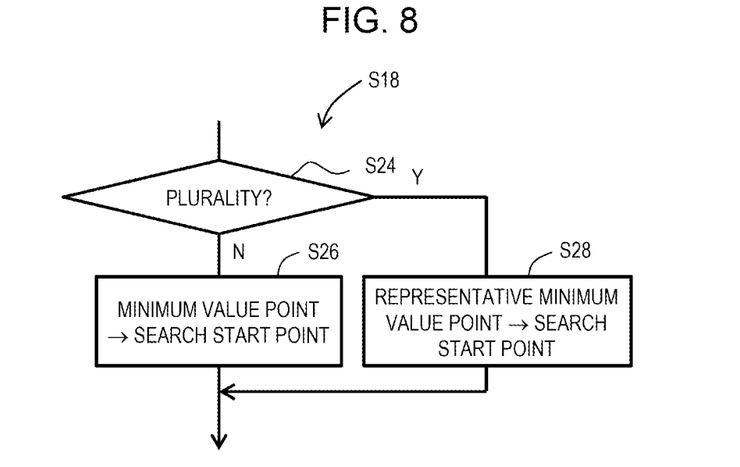
FIG. 8 is a flowchart showing a specific example of S18.

In S18, when a plurality of minimum value points are specified, the processing shown in FIG. 8 may be executed to specify one minimum value point. In S24, when it is determined that a plurality of minimum value points is detected, a representative minimum value point is specified from among the plurality of minimum value points, and a representative minimum value point is set as a search start point in S28. On the other hand, in S24, when it is determined that one minimum value point is detected, the minimum value point is determined as the search start point in S26.

In S28, it is preferable to determine whether the plurality of minimum value points is continuously or discretely located, and to change a determination rule of the search start point according to the situation. For example, when a plurality of minimum value points are continuously located, the minimum value point closest to the non-base line side among the plurality of minimum value points may be specified, and the minimum value point may be set as the search start point. When a plurality of minimum value points is discretely located, an average position thereof may be set as the search start point.

According to the above embodiment, the accuracy of tracing the Doppler waveform including the folded component is improved. According to the above embodiment, it is possible to execute the tracing method adapted to the nature of the Doppler waveform. When the detection range is set, a plurality of past search start points may be referred to. A center point and a center of gravity of the trough portion may be regarded as the minimum value point. By applying the method described above, a modification example in which the waveform portion (folded portion) on the non-base line side is deleted from the search start point on each line can be considered. The above search processing and the search processing from the base line side may be used in combination.

REFERENCE SIGN LIST

10: probe
16: tomographic image forming unit
18: Doppler waveform generation unit
20: trace unit
22: measurement unit
24: display processing unit

The invention claimed is:

1. An ultrasonic diagnostic apparatus comprising:
a Doppler waveform generator configured to generate a Doppler waveform based on Doppler information obtained by transmitting and receiving an ultrasonic wave, the Doppler waveform including luminance distributions; and
a trace circuit configured to determine, based on the Doppler waveform, a trace point for each of the luminance distributions, wherein
the trace circuit includes:
    a reference point setting circuit configured to set a reference point in a trough portion between a target portion and a folded portion included in the luminance distributions, the folded portion being a negative velocity component on a top portion of the Doppler waveform; and
    a search circuit configured to search for the trace point on a base line side of the reference point in the luminance distributions,
wherein the reference point is a search start point, and the search circuit is configured to search from the search start point to the base line side,
wherein the reference point setting circuit includes a range setting circuit configured to set a detection range in which a current search start point is detected based on a past search point,
wherein the reference point setting circuit is configured to set the current search start point by specifying a minimum luminance value within the detection range.

2. An ultrasonic diagnostic apparatus comprising:
a Doppler waveform generator configured to:
    generate a first Doppler waveform based on first Doppler information obtained by transmitting and receiving a first ultrasonic wave, the first Doppler waveform including first luminance distributions; and
    generate a second Doppler waveform based on second Doppler information obtained by transmitting and receiving a second ultrasonic wave, the second Doppler waveform including second luminance distributions;
a trace circuit configured to:
    determine a first trace point for each of first luminance distributions; and
    determine a second trace point for each of second luminance distributions
wherein the trace circuit is configured to:
    set a search start point in a trough portion between a target portion and a folded portion included in the first luminance distributions, and search the first trace point from the search start point to a base line side in the first luminance distributions, the folded portion being a negative velocity component on a top portion of the first Doppler waveform, and
    search the second trace point from an end point on an opposite side of the base line to the base line side in the second luminance distributions.

* * * * *